(12) United States Patent
Stroumpoulis et al.

(10) Patent No.: US 8,394,784 B2
(45) Date of Patent: *Mar. 12, 2013

(54) POLYSACCHARIDE GEL FORMULATION HAVING MULTI-STAGE BIOACTIVE AGENT DELIVERY

(75) Inventors: Dimitrios Stroumpoulis, Goleta, CA (US); Dustin B. Leslie, Santa Barbara, CA (US); Christopher S. Mudd, Goleta, CA (US); Ahmet Tezel, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 12/616,020

(22) Filed: Nov. 10, 2009

(65) Prior Publication Data

US 2010/0098764 A1 Apr. 22, 2010

Related U.S. Application Data

(63) Continuation-in-part of application No. 12/276,167, filed on Nov. 21, 2008.

(60) Provisional application No. 60/991,473, filed on Nov. 30, 2007.

(51) Int. Cl.
*A01N 43/04* (2006.01)
*C07H 1/00* (2006.01)

(52) U.S. Cl. .......... 514/55; 514/54; 536/55.1; 536/55.2; 536/123.1

(58) Field of Classification Search .................... 514/54, 514/55; 536/55.1, 55.2, 123.1
See application file for complete search history.

(56) References Cited

U.S. PATENT DOCUMENTS

| | | | |
|---|---|---|---|
| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,713,448 A | 12/1987 | Balazs |
| 4,716,154 A | 12/1987 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leschiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto et al. |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |

(Continued)

FOREIGN PATENT DOCUMENTS

| | | |
|---|---|---|
| CA | 949965 | 6/1974 |
| EP | 0273823 | 7/1988 |

(Continued)

OTHER PUBLICATIONS

Belda, Jose I., et al., "Hyaluronic acid combined with mannitol to improve protection against free-radical endothelial damage: Experimental Model," J.Cataract Refract Surg 2005; 31:1213-1218.

(Continued)

*Primary Examiner* — Elli Peselev

(74) *Attorney, Agent, or Firm* — Linda Fox; Stephen Donovan; Debra Condino

(57) ABSTRACT

Described herein are polysaccharide gel formulations including at least one inhibitor of polysaccharide degradation and methods of making the same. The methods described herein involve the steps of providing at least one polysaccharide and incorporating at least one inhibitor of degradation into the polysaccharide.

6 Claims, 7 Drawing Sheets

U.S. PATENT DOCUMENTS

| | | |
|---|---|---|
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg et al. |
| 7,196,180 B2 | 3/2007 | Aeschlimann |
| 7,314,636 B2 | 1/2008 | Caseres et al. |
| 7,491,709 B2 | 2/2009 | Carey |
| 7,741,476 B2 | 6/2010 | Lebreton |
| 7,902,171 B2 | 3/2011 | Reinmuller et al. |
| 8,124,120 B2 | 2/2012 | Sadozai |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leschchiner et al. |
| 2005/0181007 A1 | 8/2005 | Hunter |
| 2005/0186261 A1 | 8/2005 | Avelar |
| 2005/0227936 A1 | 10/2005 | McSwiggen et al. |
| 2005/0271729 A1 | 12/2005 | Wang |
| 2005/0287180 A1 | 12/2005 | Chen |
| 2006/0040894 A1 | 2/2006 | Hunter et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0194758 A1 | 8/2006 | Lebreton et al. |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1* | 8/2008 | Bitterman et al. ............. 514/55 |
| 2008/0207794 A1 | 8/2008 | Wright et al. |
| 2008/0241252 A1 | 10/2008 | Lyons |
| 2008/0268051 A1 | 10/2008 | Hughes et al. |
| 2008/0274946 A1 | 11/2008 | Giampapa |
| 2008/0279806 A1 | 11/2008 | Cho |
| 2009/0018102 A1 | 1/2009 | Moutet et al. |
| 2009/0022808 A1 | 1/2009 | Champion |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel et al. |
| 2009/0155362 A1 | 6/2009 | Longin |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0316683 A1 | 12/2010 | Piron |
| 2011/0034684 A1 | 2/2011 | Yokokawa |

FOREIGN PATENT DOCUMENTS

| | | |
|---|---|---|
| EP | 0416250 | 3/1991 |
| EP | 0416846 | 3/1991 |
| EP | 1247522 | 10/2002 |
| EP | 141792 | 4/2003 |
| EP | 1398131 | 3/2004 |
| EP | 1726299 | 11/2006 |
| EP | 2236523 | 10/2010 |
| FR | 2733427 | 5/2001 |
| FR | 2920000 | 2/2009 |
| FR | 2924615 | 1/2010 |
| JP | 55-153711 | 11/1980 |
| JP | 2007063177 | 3/2007 |
| WO | WO 86/00079 | 1/1986 |
| WO | WO 86/00912 | 2/1986 |
| WO | WO 92/00105 A | 1/1992 |
| WO | WO 92/20349 | 11/1992 |
| WO | WO 94/01468 | 1/1994 |
| WO | WO 94/02517 | 2/1994 |
| WO | WO 96/33751 | 1/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 01/79342 | 10/2001 |
| WO | WO 02/05753 | 1/2002 |
| WO | WO 02/06350 | 1/2002 |
| WO | WO 02/09792 | 2/2002 |
| WO | WO 02/17713 | 3/2002 |
| WO | WO 03/007782 | 1/2003 |
| WO | WO 2004/020473 | 3/2004 |
| WO | WO 2004/022603 | 3/2004 |
| WO | WO2004/073759 | 9/2004 |
| WO | WO 2004/073759 | 9/2004 |
| WO | WO 2004/092223 | 10/2004 |
| WO | WO 2005/040224 | 5/2005 |
| WO | WO 2005/067994 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2008/034176 A | 3/2008 |
| WO | WO 2008/068297 | 6/2008 |
| WO | WO 2008/072230 A | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 A | 3/2009 |

| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |

OTHER PUBLICATIONS

Intramed Mannitol 20% m/v Infusion, package insert, pp. 1-2 (2010) http://home.intekom.com/pharm/intramed/manitl20.html.
Osmitrol (generic name Mannitol),Official FDA Information, side effects and uses, pp. 1-10 (2010) http://www.drugs.com/pro/osmitrol.html.
SCULPTRA® Aesthetic (injectable poly-L-lactic acid) Directions for Use, Dermik Laboratories product insert (Jul. 2009), sanofi-aventis U.S. LLC.
Visiol, Viscoelstic gel for use in ocular surgery, (2010) p. 1 htt://www.trbchemedica.com/index.php/option=com_content&task=view &id=25&Itemid=41.
*Aesthetic Buyers Guide*, "Juvéderm Raises Standards" Jan./Feb. 2007 (5 pp.), www.miinews.com.
McPherson, et al., Development and Biochemical Characterization of Injectable Collagen, J. Dermatol Surg Oncol, 1988, 14 Supp 1.
Albano, Emanuele, et al., "Hyroxyethyl Radicals in Ethanol Hepatotoxicity," Frontiers in Bioscience 4:533-540 (1999).
Baumann et al. "JUVEDERM vs. ZYPLAST Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).
Beasley et al. :Hyaluronic acid fillers: a comprehensive review. Facial Plast. Surg. 25(2): 86-94 (2009).
Beer "Dermal fillers and combinations of fillers for facial rejuvenation." Dermatol. Clin. 27(4): 427-432 (2009).
Carlin, G., et al., "Effect of anti-inflammatory drugs on xanthine oxidase and xanthine oxidase induced depolymerization of hyaluronic acid," Agents and Actions. 16 (5):377-384 (1985).
Carruthers et al. "The science and art of dermal fillers for soft-tissue augmentation." J. Drugs Dermatol. 8(4): 335-350 (2009).
Falcone et al. "Crosslinked hyaluronic acid dermal fillers: a comparison of rheological properties." J Biomed Mater Res A. 87(1): 264-271 (2008).
Falcone et al. "Temporary polysaccharide dermal fillers: a model for persistence based on physical properties." Dermatol Surg. 35(8): 1238-1243 (2009).
Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).
Gold MH, "Use of Hyaluronic acid fillers for the treatment of the aging face." Clin. Interventions Aging 2(3): 369-376 (2007).
Goldberg "Breakthroughs in US dermal fillers for facial soft-tissue augmentation." J Cosmet Laser Ther. 11(4): 240-247 (2009).
Graefe, Hendrik, et al., "Sensitive and specific photometric determination of mannitol in human serum," Clin Chem Lab Med. 41 (8):1049-1055 (2003).
Kablik et al. "Comparative physical properties of hyaluronic acid dermal fillers." Dermatol. Surg. Suppl. 35(Suppl. 1): 302-312 (2009).
Lupo, MP., "Hyaluronic acid fillers in facial rejuvenation." Semin. Cutan. Med. Surg. 25(3): 122-126 (2006).
Orvisky, E., et al., "High-molecular-weight hyaluronan—a valuable tool in testing the antioxidative activity of amphiphilic drugs stobadine and vinpocetine," Pharm.Biomed.Anal. 16:419-424 (1997).
Prestwich, Glenn D., "Evaluating drug efficacy and toxicology in three dimensions: using synthetic extracellular matrices in drug discovery," Accounts of Chemical Research 41 (1):139-148 (2008).
Segura et al. "Crosslinked hyaluronic acid hydrogels: a strategy to functionalize and pattern." Biomaterials 26(4): 359-371 (2005).
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Tezel et al. "The science of hyaluronic acid dermal fillers." J. Cosmet. Laser Ther. 10(1): 35-42 (2008).
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Zheng et al. "In situ crosslinkable hyaluronan hydrogels for tissue engineering." Biomaterials 25(7-8): 1339-1348 (2004).
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.
Atanassoff, Peter G., et al., "The Effect of Intradermal Administration of Lidocaine and Morphine on the Response to Thermal Stimulation", Anesth Analg 1997; 84:1340-3.
Bircher, Andreas J., et al., "Delayed-type hypersensitivity to subcutaneous lidocaine with tolerance to articaine: confirmation by in vivo and in vitro tests", Contact Dermatitis 1996, 34, 387-389.
Chin, Thomas M., et al., "Allergic Hypersensitivity to Lidocaine Hydrochloride", International journal of Dermatology, vol. 19, Apr. 1980, pp. 147-148.
Desai et al., J. Pharm Sci Feb. 1995; 84 (2): 212-5.
Farley, Jon S., et al., "Diluting Lidocaine and Mepivacaine in Balanced Salt Solution Reduces the Pain of Intradermal Injection", Regional Anesthesia 19(1):48-51, 1994.
Fujinaga, Masahiko, et al., "Reproductive and Teratogenic Effects of Lidocaine in Sprague-Dawley Rats", Anesthesiology 65:626-632, 1986.
Gammaitoni, Arnold R., et al., "Pharmacokinetics and safety of continuously applied lidocaine patches 5%", Am J Health Syst Pharm, vol. 59, Nov. 15, 2002, pp. 2215-2220.
GinShiCel MH Hydroxy Propyl Methyl Cellulose, Web Page http://www.ginshicel.cn/MHPC.html, Nov. 12, 2008.
Hassan et al., Effects of Adjuvants to local anaesthetics on their duration. III. Experimental studies of hyaluronic acid. Abstract Pub Med [Acta Anesthesiol Scand. May 1985; 29(4):384-8].
Kulicke et al., "Visco-Elastic Properties of Sodium Hyaluronate Solutions," American Institue of Physics (2008).
Lamar et al., "Antifibrosis Effect of Novel Gels in Anterior Ciliary Slerotomy *ACS)," ARVO 2002 abstract.
Levy, Jaime et al., "Lidocaine hypersensitivity after subconjunctival injection", Can J Ophthalmol 2006; 41:204-6.
Mackley, et al., "Delayed-Type Hypersensitivity to Lidocaine", Arch Dermatol, vol. 139, Mar. 2003, pp. 343-346.
Matsumoto, Alan H, et al., "Reducing the Discomfort of Lidocaine Administration through pH Buffering," Journal of Vascular and Interventional Radiology, Jan.-Feb. 1994, pp. 171-175.
McCleland, Plastic Reconstructive Surg., 100(6), Nov. 1997, pp. 1466-1474.
Rehakova, Milena, et al., "Properties of collagen and hyaluronic acid composite materials and their modifications by chemical crosslinking," Journal of Biomedical Research, vol. 30, 1996, pp. 369-372 XP002590342.
Sannino et al., "Crosslinking of Cellulose Derivatives and Hyaluronic Acid with Water-Soluble Carbodiimide," Polymer 46 (2005)pp. 11206-11212.
Silver et al., "Physical Properties of Hyaluronic Acid and Hydroxypropylmethylcellulose in Solution: Evaluation of Coating Ability," Journal of Applied Biomaterials, vol. 5, 89-98 (1994).

Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.

Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.

Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.

Yun, YH et al., "Hyaluronan Microspheres for Sustained Gene Delivery and Site-Specific Targeting.", Biomaterials, vol. 25, 2004, pp. 147-157.

Adams; "An Analysis of Clinical Studies of the Uses of Crosslinked Hyaluronan, Hylan, in the Treatment of Osteoarthritis"; J. Rheumatol Suppl. ; vol. 39; pp. 16-18; Aug. 1993.

Allemann et al.; "Hyaluronic acid gel (JUVADERM) preparations in the treatment of facial wrinkles and folds"; Clinical Interventions in Aging; vol. 3, No. 4; pp. 629-634; 2008.

Bluel et al.; "Evaluation of Reconstituted Collagen Tape as a Model for Chemically Modified Soft Tissues", Biomat. Med. Dev. Art. Org.; vol. 9(1); pp. 37-46; 1981.

Capozzi et al., "Distant Migration of Silicone Gel From a Ruptured Breast Implant", Plastic and Reconstructive Surgery; vol. 62; pp. 302-303; 1978.

Champion et al., "Role of Target Geometry in Phagocytosis"; S. Proc. Nat. Acad. Sci.; vol. 103; No. 13; pp. 4930-4934; Mar. 28, 2006.

Chvapil, "Collagen Sponge: Theory and Practice of Medical Applications", J. Biomed Mater. Res., vol. II, pp. 721-741; 1977.

Clark et al., "The Influence of Triamcinolone Acetonide on Joint Stiffness in the Rat", J Bone Joint Surg; vol. 53-A; pp. 1409-1414; Oct. 1971.

Cohen et al., "Organization and Adhesive Properties of the Hyaluronan Pericellular Coat of Chrondrocytes and Epithelial Cells", Biophys J.; vol. 85; pp. 1996-2005; Sep. 2003.

Deland, "Intrathecal Toxicity Studies with Benzyl Alcohol", Toxicol Appl Pharmacol; vol. 25; pp. 153-156; 1973.

Eyre et al., Top Curr. Chem., vol. 247, pp. 207-229; 2005.

Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.

Grillo et al., "Thermal Reconstitution of Collagen from Solution and the Response to Its Heterologous Implantation", JSR; vol. II, No. 1, pp. 69-82; Jan., 1962.

Hayashibara, "AA2G"; Sep. 23, 2007, http://web.archive.org/web/2007923072010/http://www.hayashibara-intl.com/cosmetics/aa2g.html.

Helliwell, "Use of an Objective Measure of Articular Stiffness to Record Changes in Finger Joints After Intra-Articular Injection of Corticosteroid", An Theum Dis; vol. 56; pp. 71-73; 1997.

Hertzberger-Ten Cate et al., "Intra-Articular Steroids in Pauciarticular Juvenile Chronic Arthritis", Type I, Eur J Pediatr; vol. 150; pp. 170-172; 1991.

Hetherington, "Potential for Patient Harm From Intrathecal Administration of Preserved Solutions", Abstract only Med J; vol. 173(3); p. 141; Aug. 2000.

Hurst, "Adhesive Arachnoiditis and Vascular Blockage Caused by Detergents and Other Chemical Irritants: an Experimental Study", J Path Bact, Vol. LXX, No. 70; pp. 167-177; 1955.

Jones et al., "Intra-Articular Hyaluronic Acid Compared to Intral-Articular Triamcinolone Hexacetonide in Inflammatory Knee Osteoarthritis", Osteoarthritis Cartilage, vol. 3; pp. 269-273; 1995.

Klein, "Skin Falling Collagen and Other Injectables of the Skin", Dermatologic Clinics; vol. 19, No. 3, pp. 491-588; Jul. 2001.

Kopp et al., "The Short-Term Effect of Intra-Articular Injections of Sodium Hyaluronate and Corticosteroid on Temporomandibular Joint Pain and Dysfunction", J.Oral Maxillofac Surg.; vol. 43; pp. 429-435; 1985.

Laeschke, "Biocompatibility of Microparticles into Soft Tissue Fillers", Semin. Cutan. Med. Surg., vol. 23; pp. 214-217; 2004.

Mancinelli et al., "Intramuscular High-Dose Triamcinolone Acetonide in the Treatment of Severe Chronic Asthma ", West J. Med; vol. 167(5); pp. 322-329; Nov. 1997.

McCarty et al., "Inflammatory Reaction After Intrasynovial Injection of Microcrystalline Adrenocorticosteroid Esters", Arthritis and Rheuymatism; vol. 7(4); pp. 359-367; 1964.

Rosenblatt et al., "The Effect of Collegen Fiber Size Distribution on the Release of Proteins from Collagen Matrices by Diffusion", J. Controlled Rel., vol. 9; pp. 195-203; 1989.

Rosenblatt et al., "Chain Rigidity and Diffusional Release in Biopolymer Gels", Proceed. Inter. Symp. Control. Rel. Bioact. Mater.; vol. 20; pp. 264-265; 1993; Controlled Release Society, Inc.

Selvi et al, "Arthritis Induced by Corticosteroid Crystals", J. Rheumatology; vol. 34:3; 1 page; 2004.

Zulian et al., "Triamcinolone Acetonide and Hexacetonide Intra-Articular Treatment of Symmetrical Joints in Juvenile Idiopathis Arthritis: a Double-Blind Trial", Rheumatology; vol. 43; No. 10; pp. 1288-1291; 2004.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Cui et al; "The Comparison of Physicochemical Properties of Four Cross-Linked Sodium Hyaluronate Gels with Different Cross-Linking Agents"; Advanced Matierals Research; vols. 396-398; pp. 1506-1512; 2012.

Lindvall et al.; "Influence of Various Compounds on the Degradation of Hyaluronic Acid by a Myeloperoxidase System"; Chemical-Biological Interactions; vol. 90; pp. 1-12; 1994.

Weidmann; "New Hyaluronic Acid Filler for Subdermal and Long-Lasting Volume Restoration of the Face"; European Dermatology; pp. 65-68; 2009.

Skardal et al. "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

Remington's Pharmaceutical Science Mac Publishing Company, Easton, PA 16th Edition 1980; 1-page.

Millay et al.; "Vasoconstrictors in Facial Plastic Surgery"; Archives of Otolaryngology—Head & Neck Surgery; vol. 117; pp. 160-163; Feb. 1991.

Wahl, "European Evaluation of a New Hyaluronic Acid Filler Incorporating Lidocaine", Journal of Cosmetic Dermatology; vol. 7; pp. 298-303; 2008.

* cited by examiner

POLYSACCHARIDE GEL FORMULATION HAVING MULTI-STAGE BIOACTIVE AGENT DELIVERY

CROSS REFERENCE TO RELATED APPLICATIONS

This application is a continuation-in-part of application Ser. No. 12/276,167 filed Nov. 21, 2008, which claims the benefit of U.S. provisional patent application No. 60/991,473, filed Nov. 30, 2007, the entire disclosures of which are incorporated herein by reference.

BACKGROUND

Polysaccharides are relatively complex carbohydrates. They are polymers made up of many monosaccharides joined together by glycosidic bonds. They are therefore large, often branched, macromolecules. Polysaccharides, especially hyaluronic acid (HA), have been useful in cosmetic and medical applications. These polymers have been used, for example, as fillers in soft tissue augmentation.

A polysaccharide such as HA is found naturally in many tissues of the body, such as, but not limited to, skin, cartilage, and the vitreous humor. It is therefore well suited to biomedical applications targeting these tissues. HA can be used in eye surgery (i.e., corneal transplantation, cataract surgery, glaucoma surgery and surgery to repair retinal detachment). HA is also used to treat osteoarthritis of the knee. Such treatments, called visco-supplementation, are administered as a course of injections into the knee joint and are believed to supplement the viscosity of the joint fluid, thereby lubricating the joint, cushioning the joint, and producing an analgesic effect. It has also been suggested that HA has positive biochemical effects on cartilage cells. Oral use of HA has been lately suggested, although its effectiveness needs to be demonstrated. At present, there are some preliminary clinical studies that suggest that oral administration of HA has a positive effect on osteoarthritis.

Due to its high biocompatibility and its common presence in the extracellular matrix of tissues, HA can be used as a biomaterial scaffold in tissue engineering research. In some cancers, HA levels correlate well with malignancy and poor prognosis. HA is thus often used as a tumor marker for prostate and breast cancer. It may also be used to monitor the progression of the disease. HA may also be used postoperatively to induce tissue healing, notably after cataract surgery. Current models of wound healing propose that larger polymers of HA appear in the early stages of healing to physically make room for white blood cells, which mediate the immune response.

Residing in the extracellular space, HA functions as a space-filling, structure stabilizing, and cell protective molecule with uniquely malleable physical properties and superb biocompatibility. HA matrices are extremely viscoelastic while preserving a high level of hydration. A strong correlation exists between the water content in the skin and levels of HA in dermal tissue. As human skin ages, there are known alterations in HA content and metabolism. With these changes, there is a significant deterioration in the mechanical properties of the skin. There appears to be a relationship between youthful skin and the presence of a strong HA network in the intercellular matrix.

Non-cross-linked as well as cross-linked polysaccharide chains, such as HA, are subject to degradation through different pathways; (e.g. enzymatic, free radical) thus limiting the polymer's longevity in vivo. It is, therefore, important to develop methods and compositions that decrease the rate of natural decomposition and increase the product's persistence in vivo. There remains an unmet need for a polysaccharide formulation that has increased longevity by being resistant to degradation.

Additionally, there is a long felt need in the art for polysaccharide formulations that provide a controlled release of biologically active agents to the surrounding tissues for periods extending after implantation. Such bioactive agents can be used to treat some of the side effects of the polysaccharide formulations themselves.

There are numerous disclosures of HA including degradation prevention and methods of delivering HA formulations in the art, including, but not limited to: U.S. Publication No. 2009/0036403 (cross-linked HA compositions including polyethylene glycol); U.S. Publication No. 2009/0030367 (needle-free injection device for delivering HA formulations); and U.S. Publication No. 2009/0022808 (coated HA particles for soft tissue augmentation).

SUMMARY

Described herein are soft tissue augmentation systems, generally polysaccharide based polymer systems, with increased longevity, increased degradation time, and/or sustained release of at least one biologically active agent in vivo. Generally, the systems include the ability to deliver one or more biologically active agents in one or more stages, levels, timeframes and/or profiles.

The soft tissue augmentation systems described herein comprise a polysaccharide matrix having polysaccharide particles dispersed therein, wherein the matrix and/or the particles further comprise at least one biologically active agent and where the matrix and/or the particles control the release of the at least one biologically active agent from the matrix and/or the particles and into the soft tissue. The systems can release a biologically active agent at a first rate and the particles release a biologically active agent at a second rate. In one embodiment, the first rate is faster than the second rate.

In another embodiment, the particles comprise populations of different particles wherein each population has a different release rate than other particle populations.

In yet another embodiment, the matrix and the particles release the same biologically active agent or release different biologically active agents. In some embodiments, the biologically active agent is selected from the group consisting of enzyme inhibitors, anesthetic agents, medicinal neurotoxins, antioxidants, anti-infective agents, anti-inflammatory agents, ultraviolet (UV) light blocking agents, dyes, hormones, immunosuppressants, and combinations thereof. In other embodiments, the inhibitor is tannic acid or chondroitin sulfate A (CSA) and the anesthetic agent is lidocaine.

In another embodiment, the matrix comprises a polysaccharide selected from the group consisting of hyaluronic acid (HA), o-sulfated HA, dextran, dextran sulfate, cellulose, chondroitin sulfate, heparin, heparin sulfate, alginate, keratin sulfate, chitosan, and cellulose. Further, the matrix can be chemically cross-linked, physically cross-linked or uncross-linked.

In one embodiment, the particles comprise chitosan physically cross-linked with tripolyphosphate and coated with alginate. In another embodiment, the particles comprise alginate physically cross-linked with calcium and stabilized with chitosan. In other embodiments, the particles are between about 10 μm and about 100 μm in diameter.

Further described herein are soft tissue augmentation systems comprising CSA-containing, alginate-coated chitosan particles dispersed in a cross-linked HA matrix wherein the final concentration of CSA is between about 1 mg/mL and about 10 mg/mL.

Even further still, described herein are soft tissue augmentation systems comprising CSA-containing, alginate-coated chitosan particles dispersed in a cross-linked HA matrix wherein the final concentration of CSA is between about 1 mg/mL and about 10 mg/mL and wherein the HA matrix further contains from about 1 mg/mL to about 10 mg/mL of tannic acid.

Also described herein are soft tissue augmentation systems comprising tannic acid-containing, alginate-coated chitosan particles dispersed in a cross-linked HA matrix wherein the final concentration of tannic acid is between about 0.1 mg/mL and about 2 mg/mL.

In some embodiments, the soft tissue augmentation systems further comprise lidocaine in the HA matrix.

DEFINITION OF TERMS

Figure 1:
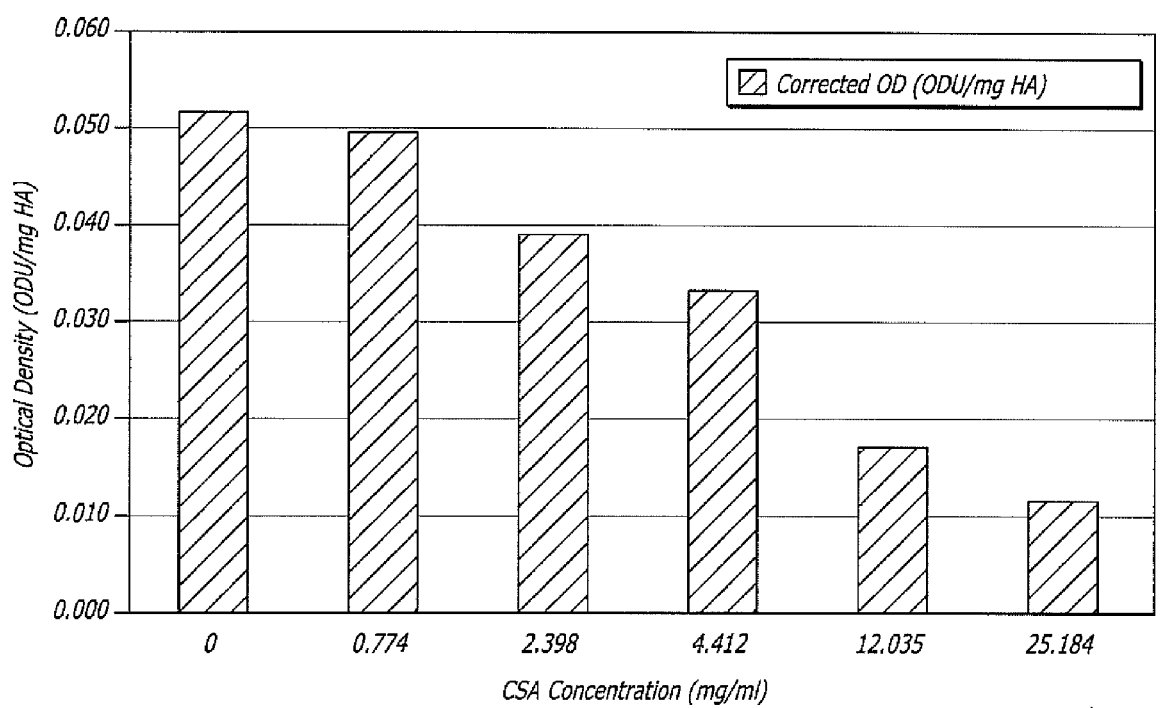
FIG. 1 graphically illustrates the extent of enzymatic degradation of polysaccharide gels including chondroitin sulfate A (CSA) using a colorimetric assay.

As used herein, "about" means approximately or nearly and in the context of a numerical value or range set forth herein means +/−10% of the numerical value or range recited or claimed.

As used herein, "carrier," "inert carrier," and "acceptable carrier" may be used interchangeably and refer to a carrier which may be combined with the presently disclosed systems in order to provide a desired composition. Those of ordinary skill in the art will recognize a number of carriers that are well known for making specific remedial pharmaceutical and/or cosmetic compositions.

As used herein, "cosmetic" is an adjective referring to improving the appearance of a surface or covering defects. Typically, cosmetic compositions can be used to improve aesthetic rather than functional aspects of a surface. Most commonly, cosmetic compositions are formulated for application as a health and beauty treatment or for affecting personal appearance of the body, for example, keratinous surfaces such as skin, hair, nails, and the like.

As used herein, "cosmetically acceptable carrier" refers to a material which is suitable for application to keratinous surfaces or other areas of the body. Upon application, cosmetically acceptable carriers are substantially free of adverse reactions with skin and other keratinous surfaces. For example, the cosmetic carriers may take the form of fatty or non-fatty creams, milky suspensions or emulsion-in-oil or oil-in-water types, lotions, gels or jellies, colloidal or non-colloidal aqueous or oily solutions, pastes, aerosols, soluble tablets or sticks.

As used herein, "formulation" and "composition" may be used interchangeably and refer to a combination of elements that is presented together for a given purpose. Such terms are well known to those of ordinary skill in the art.

As used herein "molecular weight ($M_w$)" refers to the sum of the atomic weights of the atoms in a molecule. For example, that of methane ($CH_4$) is 16.043 g/mol, the atomic weights being carbon=12.011 g/mol, hydrogen=1.008 g/mol. A Dalton (Da) is a unit of mass equal to $1/12$ the mass of $^{12}O$ and one million Da can be notated as 1 MDa.

DETAILED DESCRIPTION

Described herein are soft tissue augmentation systems and compositions with increased longevity, increased degradation time, and/or sustained release of at least one biologically active agent in vivo. This increase in degradation time can be provided by the incorporation of molecules that act as inhibitors to degradation. The systems themselves are generally polysaccharide based. Generally, the systems include the ability to deliver one or more biologically active agents in one or more stages, levels, timeframes and/or profiles.

The soft tissue augmentation systems described herein comprise a polysaccharide matrix having polysaccharide particles dispersed therein, wherein the matrix and/or the particles further comprise at least one biologically active agent and where the matrix and/or the particles control the release of the at least one biological agent from the matrix and/or the particles and into the soft tissue.

The soft tissue augmentation systems described herein generally relate to new multi-action polymer systems that provide soft tissue augmentation (e.g. lift and wrinkle correction, etc.), resist various in-vivo degradation pathways (e.g. enzymatic, free radical degradation, etc.) and provide controlled drug delivery (e.g. to relieve injection pain, bruising and bleeding, etc.). These features of the systems described herein are different from fillers currently on the market which are typically limited by their low degradation resistance, increased susceptibility to lymphatic removal and general patient discomfort during injection, and for the first few weeks following injection.

One aspect of the present disclosure relates to soft tissue augmentation systems comprising at least one polysaccharide or a polysaccharide matrix. "Polysaccharide" as used herein refers to a polymer of more than two monosaccharide molecules, of which the monosaccharides can be identical or different. The polysaccharides making up the matrices described herein be chemically cross-linked, physically cross-linked or uncross-linked. The polysaccharides used herein can be, but are not limited to, HA, cellulose, chitosan, a-sulfated HA, dextran, dextran sulfate, chondroitin sulfate, dermatan sulfate, keratin sulfate, heparin, heparin sulfate, and alginate. The systems further include polysaccharide particles that can be physically or chemically crosslinked and are dispersed and/or entrapped within the polymer matrix.

The polysaccharides described herein can be cross-linked using a cross-linking agent known to be suitable for crosslinking polysaccharides and their derivatives via their hydroxyl groups. Suitable cross-linking agents include but are not limited to, for example, 1,4-butanediol diglycidyl ether (or 1,4-bis(2,3-epoxypropoxy)butane or 1,4-bisglycidyloxybutane, all of which are commonly known as BDDE), 1,2-bis(2,3-epoxypropoxy)ethylene and 1-(2,3-epoxypropyl)-2,3-epoxycyclohexane. The use of more than one cross-linking agent or a different cross-linking agent is not excluded from the scope of the present disclosure. In one embodiment, the cross-linking agent comprises or consists of BDDE.

The polymer systems generally are designed to provide volume correction, controlled release of biologically active agents, or bioactive agents, and to be able to retain the polysaccharide particles within the matrix. The polysaccharide particles are designed to provide structure, longer lasting correction of the soft tissue and sustained controlled release of active agents. As such, the systems described can provide in some cases at least two levels of biologically active agent release. The first level of release can be from the polymer network itself. This release is generally from biologically active agent(s) trapped within the polymer network. The second level of release can be from the polymer particles associated with the polymer network.

One advantage of having multiple levels of release from a polymer system as described herein is better control over the bioactive agent release timing. For example, freshly implanted materials are subject to an initial surge of attack by the immune system that can be effectively fended by a fast release mechanism of degradation inhibitors and anti-oxidants. Over time, however, the implanted material is subject to a milder but persistent immune attack that can be better countered by a sustained release mechanism.

The systems described herein therefore include a polymer matrix designed to provide a fast initial release with polymer particles providing a longer lasting sustained secondary release. The latter is achieved by the high stability and slow biodegradation profile of the polymer particles. In one embodiment, a biologically active agent such as an enzyme inhibitor or inhibitor of degradation (e.g. chondroitin sulfate, tannic acid, etc.) is mixed with the polymer network and also incorporated in or coated onto the polymer particles. The presence of the inhibitor inside and/or outside of the particles establishes a diffusion equilibrium that ensures a long shelf-life for the system.

Then, upon implantation, a fast release of the bioactive agents from the polymer network can provide an initial protection from the inflammatory reaction for example. This fast release activates a second stage release from the polymer particles by creating a concentration gradient along the particle surface. Release is further propagated as the polymer particles degrade in vivo. The slower second stage release provides a longer supply of the bioactive agents to the polymer network. If the bioactive agent is an inhibitor of degradation, the compositions would thereby be ensured a sustained degradation protection. In another embodiment, the enzyme inhibitor is supplemented or substituted by antioxidants (e.g. ascorbic acid, etc.) or drug molecules (e.g. lidocaine, epinephrine, etc.).

In another embodiment, the polymer particles are made by a physical cross-linking process linking chitosan with tripolyphosphate (TPP) and further coated with alginate. In yet another embodiment, the polymer particles are made by a physical cross-linking process linking alginate with calcium and further stabilized with chitosan. The resulting particles have properties making them ideal for inclusion in dermal filler compositions. For example, the particles are biocompatible/biodegradable, flexible (e.g. to facilitate extrusion through a fine needle), toxic cross-linker free, smooth textured (e.g. for increased biocompatibility), tunable in size (e.g. to tackle lymphatic removal and migration), efficient carriers of small and larger active molecules (e.g. tannic acid, lidocaine, chondroitin sulfate, epinephrine, etc.), very stable in vitro with an excellent retention profile and tunable in active molecule retention time (e.g. by adjusting the chitosan:TPP:alginate ratio).

The particles themselves can be of an appropriate size for incorporation into a polymer matrix as described herein and useful in a system as described herein. For example, the particles are between about 1 µm and about 1000 µm in diameter. In other embodiments, the particles have diameters between about 10 µm and about 100 µm or about 25 µm and about 75 µm.

The bioactive agent incorporated into the systems can be selected from the group consisting of inhibitors, anesthetic agents, medicinal neurotoxins, antioxidants, anti-infective agents, anti-inflammatory agents, ultraviolet (UV) light blocking agents, dyes, hormones, immunosuppressants, and combinations thereof.

In one embodiment, the particles or polymer matrix further comprise at least one inhibitor, for example an inhibitor of degradation. Inhibitors are molecules that act by targeting and neutralizing specific degradation mechanisms such as enzymatic and free radical degradation. Molecules that display inhibitory activity include but are not limited to glycosaminoglycans (GAGs), (e.g. heparin, heparan sulfate, dermatan sulfate, chondroitin sulfate, chondroitin sulfate A (GSA), a-sulfated HA, linamarin and amygdalin), antioxidants (e.g. ascorbic acid, melatonin, vitamin C and vitamin E), proteins (e.g. serum hyaluronidase inhibitor) and fatty acids (e.g. saturated $C_1$ to $C_{22}$ fatty acids).

Inhibitors are typically molecules orders of magnitude smaller than cross-linked polysaccharide polymers. Due to their small size and higher diffusivity, they are prone to fast adsorption in vivo that could potentially limit their performance. One method of increasing the local half-life of such molecules in vivo is to chemically graft them to the polysaccharide polymer network and deliver them simultaneously. One disadvantage of this method is that the bound molecule may display significantly lower activity compared to the unbound one.

In one embodiment, the particles or a polymer matrix further comprise at least one anesthetic. The at least one local anesthetic can be selected from the group of ambucaine, amolanone, amylocalne, benoxinate, benzocaine, betoxycaine, biphenamine, bupivacaine, butacaine, butamben, butanilicaine, butethamine, betoxycaine, carticaine, chloroprocaine, cocaethylene, cocaine, cyclomethycaine, dibucaine, dimethisoquin, dimethocaine, diperodon, dicyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In one embodiment, the at least one anesthetic agent is lidocaine, such as in the form of lidocaine HCl. The systems and compositions described herein may have a lidocaine concentration of between about 0.1% and about 5% by weight of the composition, for example, about 0.2% to about 1.0% by weight of the composition. In one embodiment, the composition has a lidocaine concentration of about 0.3% by weight (w/w %) of the composition. The concentration of lidocaine in the compositions described herein can be therapeutically effective meaning the concentration is adequate to provide a therapeutic benefit without inflicting harm to the patient.

Further examples of biologically active agents include, but are not limited to, anti-itch, anti-cellulite, anti-scarring, and anti-inflammatory agents. Anti-itch agents can include methyl sulphonyl methane, sodium bicarbonate, calamine, allantoin, kaolin, peppermint, tea tree oil and combinations thereof. Anti-cellulite agents can include forskolin, xanthine compounds such as, but not limited to, caffeine, theophylline, theobromine, and aminophylline, and combinations thereof. Anti-scarring agents can include IFN-y, fluorouracil, poly (lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine and combinations thereof.

In one embodiment, the system includes a tannic acid enzyme inhibitor or a chondroitin sulfate A (CSA) enzyme inhibitor and lidocaine. Lidocaine, or an alternate anesthetic can be used in a given formation to alleviate some or substantially all of the pain associated with injection of a viscous dermafiller. A slow release of an anesthetic can be useful to allow for residual pain relief from the injected formulation.

The biologically active agent can be present in the particles or the matrix or both at a concentration in the range of about 0.0001% to about 99% by wt, about 0.001% to about 75% by weight, about 0.01% to about 60% by weight, about 1% to about 50% by weight, about 1% to about 40% by weight, about 1% to about 30% by weight, about 1% to about 20% by weight, about 10% to about 20% by weight, about 20% to about 30% by weight 0.0001% to about 0.01% by weight, about 0.0001% to about 0.1% by weight, about 0.0001% to about 1% by weight, about 0.001% to about 1% by weight, about 0.01% to about 1% by weight, or about 1% to about 10% by weight.

In other embodiments, the concentration of biologically active agent present in the particles or the matrix or both is in a range of about 0.001 mg/mL to about 100 mg/mL, about 0.01 mg/mL to about 10 mg/mL, about 1 mg/mL to abut 10 mg/mL, about 2 mg/mL to about 5 mg/mL or about 0.1 mg/mL to about 2 mg/mL.

In one embodiment, systems release one or more bioactive agents at different rates. For example, the matrix releases a biologically active agent at a first rate and the particles release a biologically active agent at a second rate. In one example embodiment, the first rate is faster than the second rate.

In another embodiment, the particles comprise populations of different particles wherein each population has a different release rate than other particle populations. For example, particles of different sizes or shapes can have different release rates.

In some embodiments, the polymer matrix and the associated particles release the same biologically active agent. In other embodiments, the biologically active agent is different in the matrix and the particles.

Another aspect of the present disclosure relates to methods of producing polysaccharide formulations having the ability to provide delivery of at least one level of bioactive agent. These methods provide polysaccharides and associate a bioactive agent with the polysaccharide.

Non-cross-linked as well as cross-linked polysaccharide chains are subject to degradation through different pathways (e.g. enzymatic, free radical) that often limits the polymer's longevity in vivo. It is therefore important to develop ways that decrease the rate of this natural decomposition process and increase the product's persistence in tissues.

One method for achieving increased polymer, e.g. polysaccharide, persistence is to encapsulate biologically active agents such as inhibitor molecules within the polysaccharide polymer matrix itself or into particles associated within the matrix that would enable local (injection site), sustained and controlled release of the inhibitors. This would also allow avoidance of the natural degradation mechanisms. The present encapsulation methods provide a constant supply of biologically active agent for example, degradation inhibitors, to the polysaccharide polymer matrix over a period of weeks.

In other embodiments, a constant supply of bioactive agent is provided over a period of months. One method of encapsulation is to incorporate the bioactive agents within the polysaccharide polymer matrix either by adsorption or by an encapsulation process. In the latter case, the bioactive agents are allowed to mix with the polysaccharide matrix at a highly hydrated state, followed by dehydration of the matrix to control the release kinetics (e.g. final swelling ratio of the polymer). A highly hydrated state corresponds to an HA concentration that is less than about 20 mg/mL.

Another aspect of the present disclosure relates to a polysaccharide formulation comprising a polysaccharide matrix and polysaccharide particles dispersed within the matrix and at least one bioactive agent, and further comprising a biocompatible or biodegradable vessel wherein the inhibitor is inside or part of the vessel. Such vessels can be composed of non-covalently or covalently linked self-assembled molecules such as liposomes, micelles, and polymerized vesicles.

A liposome is a vesicle composed of one or more bilayer membranes formed of naturally-derived phospholipids with mixed lipid chains (such as egg phosphatidylethanolamine), or of pure surfactant components like dioleoylphosphatidylethanolamine (DOPE). Liposomes, usually but not by definition, contain a core of aqueous solution; lipid structures that contain no aqueous material are called micelles. A micelle is an aggregate of surfactant molecules dispersed in a liquid colloid. A typical micelle in aqueous solution forms an aggregate with the hydrophilic "head" regions in contact with surrounding solvent, sequestering the hydrophobic lair regions in the micelle center. This type of micelle is known as a normal phase micelle (oil-in-water micelle). Inverse micelles have the headgroups at the centre with the tails extending out (water-in-oil micelle). Micelles are often approximately spherical in shape, however, other forms, including shapes such as ellipsoids, cylinders, and bilayers are also possible. The shape and size of a micelle is a function of the molecular geometry of its surfactant molecules and solution conditions such as surfactant concentration, temperature, pH, and ionic strength. The process of forming micelles is known as micellisation and forms part of the phase behavior of many lipids according to their polymorphism.

Another aspect of the present disclosure relates to a method for producing a polysaccharide formulation having reduced degradation and bioactive agent release comprising the steps of 1) providing a polysaccharide, 2) incorporating an inhibitor and at least one bioactive agent into a biocompatible or biodegradable particle or vessel and 3) combining said polysaccharide and particle into the formulation. This method of encapsulation thus incorporates the inhibitors and bioactive agents into biocompatible and biodegradable particles that could be delivered at the same time with the polysaccharide. In the case where the particles are vessels, they can be composed of non-covalently or covalently linked self-assembled molecules (e.g. micelles, liposomes, and polymerized vesicles). Self-assembly is a term used herein to describe processes in which a disordered system of pre-existing components forms an organized structure or pattern as a consequence of specific, local interactions among the components themselves, without external direction.

An additional advantage of the proposed formulation is the increased tune-ability of the final product's rheological properties. Cross-linked polysaccharide formulations typically have high viscosity and require considerable force to extrude through a fine needle. Uncross-linked polysaccharides are often used as lubricants to facilitate this extrusion process. However, especially in HA dermal fillers, uncross-linked HA does not contribute to the persistence of the final product in vivo. In fact, the more cross-linked HA is replaced by uncross-linked HA to tune the rheological properties of the dermal filler (for a fixed total HA concentration), the lower the degradation resistance of the product will be. As such, uncross-linked GAGs that are also inhibitors to degradation (e.g. chondroitin sulfate, o-sulfated hyaluronic acid) can be used both to extend the longevity and improve the rheological properties of the final product.

In one embodiment, the systems described herein are dermal fillers which can be used to treat moderate to severe facial wrinkles and folds such as nasolabial folds (those lines that extend from the nose to the corners of the mouth). Dermal fillers can be a gel implant that includes HA, a natural complex sugar that bolsters skin elasticity, providing a smooth and supple appearance. It is biocompatible and can supplement the body's natural HA, which aging can deplete.

A dermal filler, or dermafiller, can be injected with a syringe into the mid to deep dermis of the face. The dermis is the subsurface skin layer that contains connective tissue, nerve endings, sweat and oil glands, and blood vessels. Dermal fillers can improve the skins appearance by lifting and adding volume to the wrinkles and folds in the treatment area.

Another aspect of the present disclosure relates to a cosmetic composition comprising the present systems, a cosmetic carrier, and an additional active ingredient. The cosmetic active ingredients may include but are not limited to antioxidants, vitamins, and moisturizers.

The presently described systems can be formulated as part of a pharmaceutical composition optionally including one or more agents such as, without limitation, emulsifying agents, wetting agents, sweetening or flavoring agents, tonicity adjusters, preservatives, buffers antioxidants and flavonoids. Tonicity adjustors useful in a pharmaceutical composition of the present disclosure include, but are not limited to, salts such as sodium acetate, sodium chloride, potassium chloride, mannitol or glycerin and other pharmaceutically acceptable tonicity adjusters. Preservatives useful in the pharmaceutical compositions described herein include, without limitation, benzalkonium chloride, chlorobutanol, thimerosal, phenyl mercuric acetate, and phenyl mercuric nitrate. Various buffers and means for adjusting pH can be used to prepare a pharmaceutical composition, including but not limited to, acetate buffers, citrate buffers, phosphate buffers and borate buffers. Similarly, antioxidants useful in pharmaceutical compositions are well known in the art and includes for example, sodium metabisulfite, sodium thiosulfate, acetylcysteine, butylated hydroxyanisole and butylated hydroxytoluene. Flavonoids are compounds found in plants that are well known to have diverse beneficial biochemical and antioxidant effects. Subcategories of flavonoids include: flavones, flavanols, flavanones and flavanonols. Examples of flavonoids include: luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannis, condensed tannis, and hydrolysable tannis. It is understood that these and other substances known in the art of pharmacology can be included in a pharmaceutical composition of the invention.

Some of the advantages of the present systems are illustrated below using examples which describe the preparation of an HA dermafiller formulation according to the methods described herein, the preparation of an HA dermafiller formulation according to the prior art and a comparison thereof.

Example 1

Preparation of a HA Filling Gel According to the Present Disclosure

One to five grams of polysaccharide filler with a HA concentration of 24 mg/mL, about a 6% degree of cross-linking and a G' of about 180 (JUVÉDERM® 24HV, (Allergan Inc., Irvine, Calif.)) were mixed with 1000 µL of a phosphate buffered saline (PBS) solution (pH ~7) that was supplemented with 10-200 mg of chondroitin sulfate A (CSA–$M_w$=5,000-120,000 Da). The mixture was mechanically homogenized.

Example 2

Preparation of a HA Filling Gel by the Process of the Prior Art

One to five grams of polysaccharide filler with a HA concentration of 24 mg/mL, about a 6% degree of cross-linking and a G' of about 180 Pa (JUVÉDERM® 24HV) was mixed with 1000 µL of PBS such that the final HA concentration was the same as in Example 1. The mixture was mechanically homogenized.

Example 3

An Alternative Preparation of a Hyaluronic Acid Filling Gel According to the Present Disclosure One to five grams of a HA based polysaccharide filler with a HA concentration of 24 mg/mL, about a 6% degree of cross-linking and a G' of about 170 Pa (JUVÉDERM® 30) was mixed with 50 µL of PBS solution (pH ~7) that was supplemented with 1-20 mg of tannic acid (TA–$M_w$=800-4,000 Da). The mixture was mechanically homogenized.

Example 4

An Alternative Preparation of a Hyaluronic Acid Filling Gel by the Process of the Prior Art One to five grams of a HA based polysaccharide filler with a HA concentration of 24 mg/mL, about a 6% degree of cross-linking and a G' of about 170 Pa (JUVÉDERM® 30) was mixed with 50 µL of PBS such that the final HA concentration was the same as in Example 3. The mixture was mechanically homogenized.

Example 5

Preparation of a Hyaluronic Acid Filling Gel According to the Present Disclosure One gram of sodium hyaluronate fibers (NaHA, $M_w$=0.3-3 MDa) was mixed with 5-10 g of 1% sodium hydroxide solution and the mixture was left to hydrate for 1-5 hrs.

Fifty to 200 mg of 1,4-butanediol diglycidyl ether (BDDE) were added to the NaHA gel and the mixture was mechanically homogenized.

The mixture was then placed in a 40-70° C. oven for 1-4 hrs.

The resulting cross-linked hydrogel was neutralized with an equimolar amount of hydrochloric acid (HCl) and swelled in PBS (pH ~7).

Ten to 200 mg of CSA ($M_w$=5,000-120,000 Da) were added and the hydrogel was mechanically homogenized.

Example 6

Preparation of an Hyaluronic Acid (HA) Filling Gel by the Process of the Prior Art One gram of NaHA ($M_w$=0.3-3 MDa) was mixed with 5-10 g of 1% sodium hydroxide solution and the mixture was left to hydrate for 1-5 hrs.

Fifty to 200 mg of BDDE (same HA to cross-linker molar ratio as in Example 5) were added to the NaHA gel and the mixture was mechanically homogenized.

The mixture was then placed in a 40-70° C. oven for 1-4 hrs.

The resulting cross-linked hydrogel was neutralized with an equimolar amount of hydrochloric acid (HCl) and swelled in PBS (pH ~7) such that the final HA concentration was the same as in Example 5. The obtained hydrogel was mechanically homogenized.

Example 7

Enzymatic Degradation Study

Colorimetric Test

The HA filling gels prepared in Examples 1 and 2, were evaluated for resistance to enzymatic degradation using the Morgan-Elson colorimetric assay. This assay was applied to estimate the extend of enzymatic degradation by measuring changes in the molecular weight of the HA chains.

Hyaluronidase (0.1-10 mg) was added to each HA formulation, incubated for 10-250 mins at 37° C. followed by addition of 0.1 mL of a 0.8 M potassium tetraborate solution and heating at 100° C. for 10 min. The samples were supplemented with 3 mL of a 10% (wt) p-dimethylaminobenzaldehyde solution in acetic acid and incubated at 37° C. for 10-120 mins. The process was repeated for each HA formulation, omitting the enzyme addition, to prepare a control sample. The change in the optical density (OD) at 585 nm between the enzymatically degraded sample and the control sample was used to quantify the extent of degradation for each formulation.

The results of the measurements made on the filling gels prepared according to the methods of the present disclosure and according to the prior art (FIG. 1) indicate that the OD values of the gels prepared by the methods of the present disclosure (Example 1: 0.774-25.184 mg/mL CSA) are lower than that of the gel prepared by the process of the prior art (Example 2: 0 mg/ml CSA). Since the OD value represents the extent of degradation, the results suggest that the gels prepared according to the present method display a 3-75% higher resistance to enzymatic degradation than the gel prepared according to the prior art. Furthermore, the resistance to enzymatic degradation was found to be dependent on the concentration of CSA.

Figure 2:
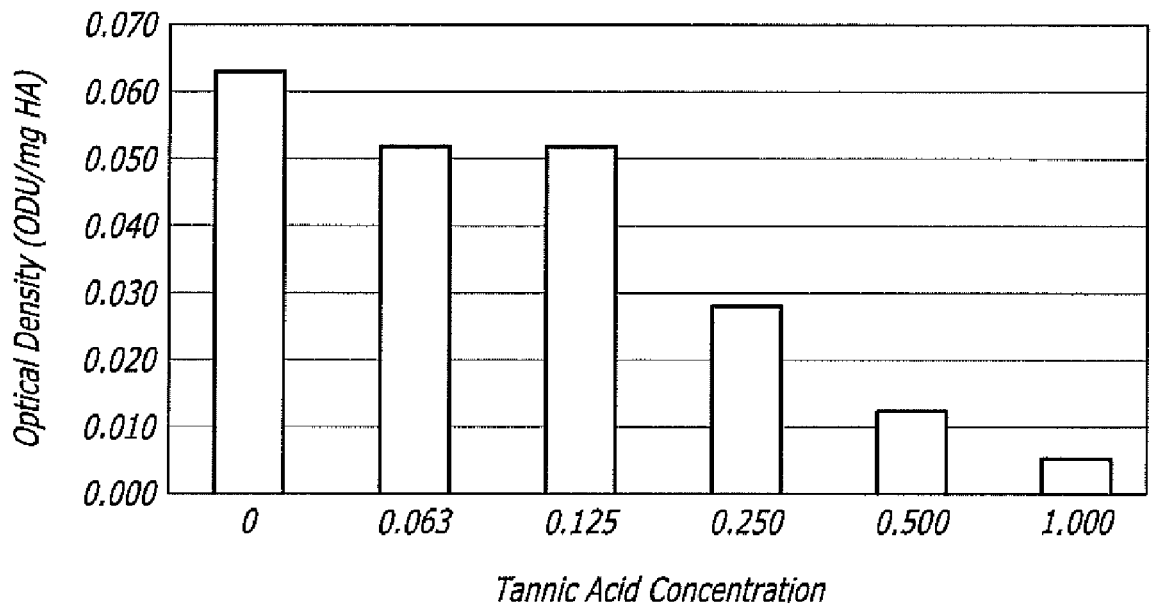
FIG. 2 graphically illustrates the extent of enzymatic degradation of polysaccharide gels including tannic acid (TA) using a colorimetric assay.

Similarly to the case of the CSA supplemented gels, the OD values of the TA supplemented gels prepared by the methods of the present disclosure, as shown in FIG. 2, (Example 3: 0.063-1.000 mg/mL TA) are lower than that of the gel prepared by the method of the prior art (Example 4: 0 mg/mL TA). Since the OD value represents the extent of degradation, the results suggest that the gels prepared according to the present description display a 15-90% higher resistance to enzymatic degradation than the gel prepared according to the prior art. Furthermore, the resistance to enzymatic degradation was found to be dependent on the concentration of TA. It can be further seen that TA has a higher inhibitory activity than CSA since it generally takes an order of magnitude less TA to obtain the same inhibition as with CSA.

Example 8

Enzymatic Degradation Study

Soluble HA Assay

The HA filling gels prepared in Examples 1 and 2, were further evaluated for resistance to enzymatic degradation by using a SEC-MALS (Size Exclusion Multi-Angle Light Scattering) based soluble HA assay. This assay was applied to quantify degradation by evaluating the soluble HA content in each sample (defined as the portion of the gel that can pass through a 0.2-1.0 μm filter). The difference in the soluble HA content, between an enzymatically degraded sample and a control sample was used to quantify the extent of degradation for each HA formulation.

The SEC-MALS tests were performed using an Agilent size exclusion chromatography system equipped with Wyatt light scattering and refractive index units. Hyaluronidase (0.1-10 mg) was added to each HA formulation, incubated for 10-250 mins at 37° C. followed by addition of 0.1 ml of a 0.8 M potassium tetraborate solution and heating at 100° C. for 10 mins. The samples were diluted in PBS, filtered through a 0.2-1.0 μm filter and injected into the SEC-MALS system. The process was repeated for each HA formulation, omitting the enzyme addition, to prepare a control sample. The soluble HA content of the enzymatically degraded sample, the control sample as well as the difference between the two is summarized in FIG. 3.

Figure 3:
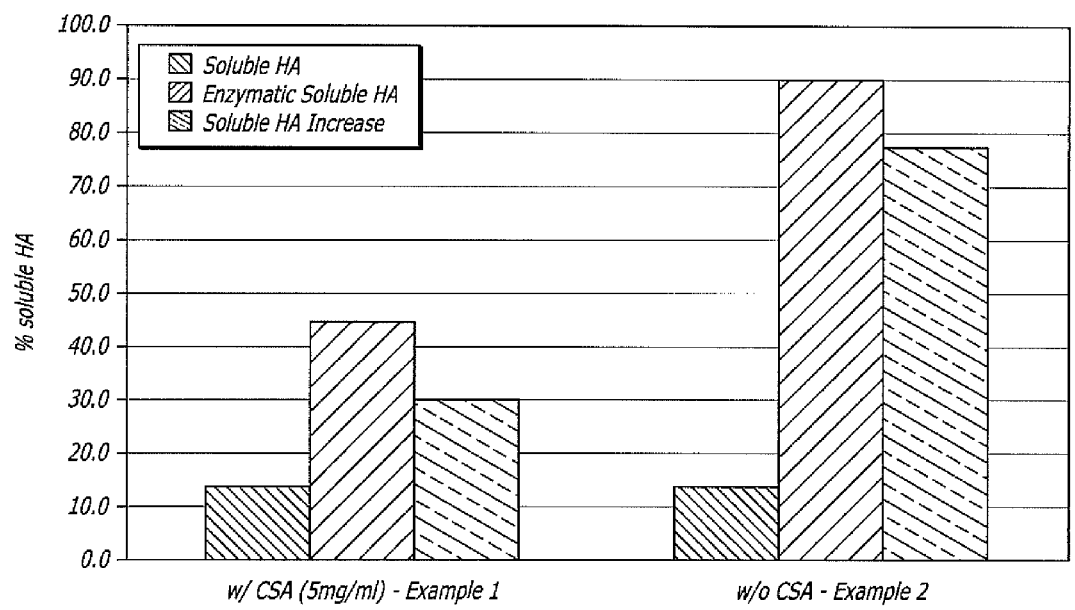
FIG. 3 graphically illustrates the extent of enzymatic degradation of polysaccharide gels both with and without CSA using a soluble HA assay.

The results shown in FIG. 3 (Enzymatic Degradation Test Results (SEC-MALS Assay)) indicate that the increase in the soluble HA content following enzymatic degradation was significantly greater in the absence of CSA. This is consistent with the results obtained using the colorimetric degradation assay (FIG. 1) and suggests that the gels prepared according to the methods of the present disclosure show a higher resistance to enzymatic degradation than the gels prepared according to the prior art.

Figure 4:
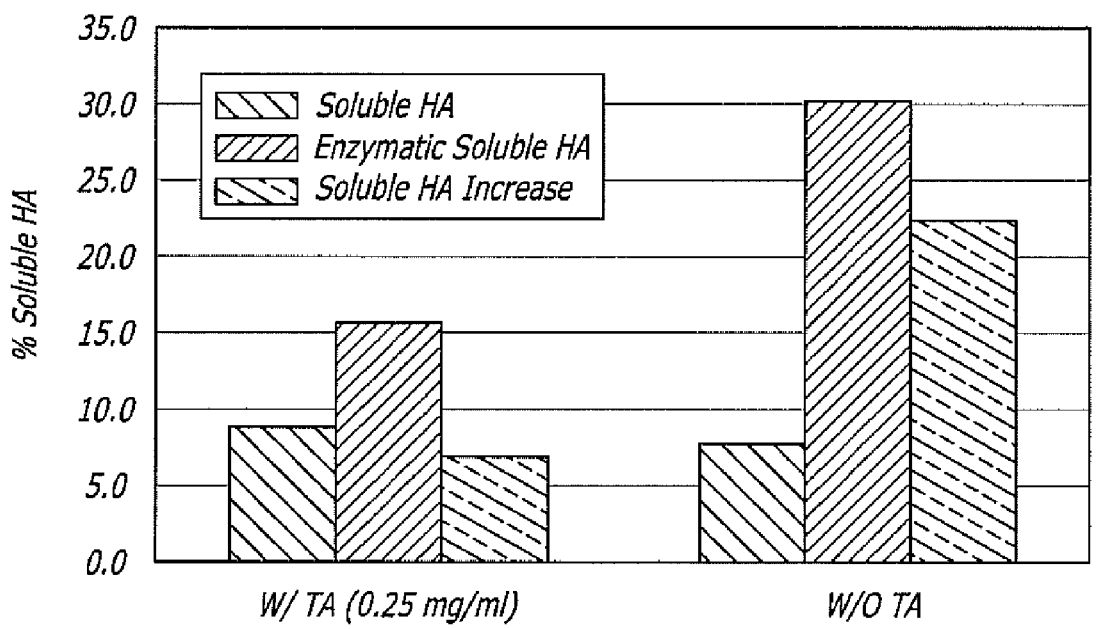
FIG. 4 graphically illustrates the extent of enzymatic degradation of polysaccharide gels both with and without TA using a soluble HA assay.

Similarly to the GSA supplemented gels, the increase in the soluble HA content of the TA supplemented gels prepared by the methods of the present description (Example 3: 0.063-1.000 mg/mL TA) was lower than that of the gels prepared by the process of the prior art (Example 4: 0 mg/mL TA). These results are in agreement with the results obtained using the colorimetric degradation assay (FIG. 4). Furthermore, it reaffirms that the inhibitory activity of TA is significantly higher than that of CSA.

Example 9

Continuous Extrusion Force Test

The rheological properties of the hyaluronic acid filling gels prepared in Examples 5 and 6 were evaluated using continuous extrusion force tests. The extrusion force test was used to determine whether the addition of CSA in HA formulations can facilitate the extrusion process by acting as a lubricant.

The extrusion force tests were performed on an Instron instrument using a 5 mL syringe with a 30 G needle. 0.5 mL of each sample was extruded at a constant rate of 50 mm/min. The peak force recorded quantifies the ease of extrusion. The compressive force as a function of the compressive extension for the two samples is shown in FIG. 5.

Figure 5:
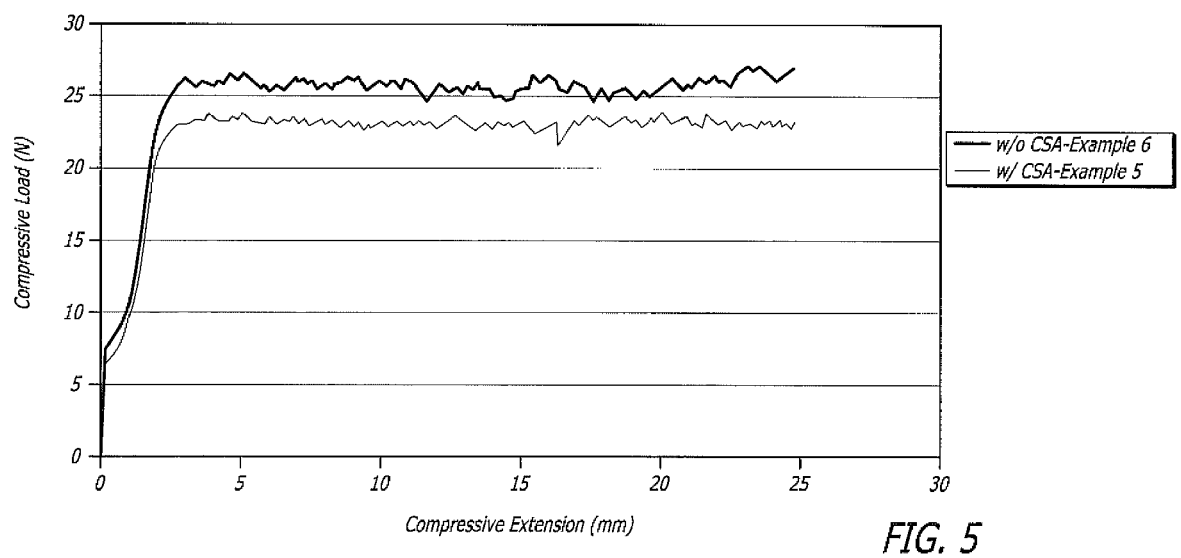
FIG. 5 graphically illustrates effects of CSA on the extrusion force of a polysaccharide gel.

The results in FIG. 5 suggest that the extrusion force recorded for the gel prepared by the methods described herein was lower than that of the gel prepared by the process of the prior art. This difference in the extrusion force is characteristic of the difference in gel hardness under flow and suggests that the CSA contained in the gel prepared by the methods described herein acts as a lubricant that facilitates flow.

Example 10

Preparation of CSA Loaded Particles According to the Present Disclosure

Uniform sized CSA loaded particles were prepared by the following process: A chitosan/CSA solution (Solution A) was prepared by mixing 10-900 mg chitosan, 1-10 mL 1 N HCl and 1-800 mg CSA with 20 mL of MilliQ $H_2O$. A dropping solution (Solution B) was prepared by mixing 0.1-10% tripolyphosphate (TPP) and 0.1-10% alginate. Solution A was loaded into disposable 3-5 mL syringes and extruded through a 27 G×½" needle at a flow rate of 0.1-10 mL/min with air flow passing over the needle tip at a rate of 1-50 mL/min. 1-10 mL of Solution A was sprayed into 5-100 mL of Solution B under stirring. The resulting particles were incubated in Solution B for 1-3 days, washed 3 times with MilliQ $H_2O$ and stored in PBS (pH=7.4) until used.

Example 11

Preparation of a CSA Particle Loaded HA Filling Gel According to the Present Description CSA loaded particles made according to Example 10 and JUVÉDERM® 30 were thoroughly mixed using two syringes connected via a female-to-female luer-lock to a final concentration of 5 mg/mL CSA.

Example 12

Preparation of a CSA Loaded HA Filling Gel According to the Prior Art

CSA and JUVÉDERM® 24HV were thoroughly mixed using two syringes connected via a female-to-female luer-lock to a final concentration of 10 mg/mL CSA.

Example 13

Alternate Preparation of a CSA Loaded HA Filling Gel According to the Prior Art

CSA and JUVÉDERM® 30 were thoroughly mixed using two syringes connected via a female-to-female luer-lock to a final concentration of 10 mg/mL CSA.

Example 14

Preparation of Tannic Acid (TA) Loaded Particles According to the Present Disclosure Uniform sized CSA loaded particles were prepared by the following process: A chitosan/TA solution (Solution C) was prepared by mixing 10-900 mg chitosan, 1-10 mL 1 N HCl and 1-800 mg tannic acid with 20 mL of MilliQ $H_2O$. A dropping solution (Solution D) was prepared by mixing 0.1-10% tripolyphosphate (TPP) and 0.1-10% alginate. Solution C was loaded into disposable 3-5 mL syringes and extruded through a 27 G×½" needle at a flow rate of 0.1-10 ml/min with air flow passing over the needle tip at a rate of 1-50 ml/min. 1-10 mL of Solution C was sprayed into 5-100 mL of Solution D under stirring. The resulting particles were incubated in Solution D for 1-3 days, washed 3 times with MilliQ $H_2O$ and stored in PBS (pH=7.4) until used.

Example 15

Preparation of a TA Particle Loaded HA Filling Gel According to the Present Description TA loaded particles made according to Example 14 and JUVÉDERM® 30 were thoroughly mixed using two syringes connected via a female-to-female luer-lock to a final concentration of 1 mg/mL TA.

Example 16

Preparation of a Tannic Acid (TA) Loaded HA Filling Gel According to the Prior Art TA and JUVÉDERM® 30 were thoroughly mixed using two syringes connected via a female-to-female luer-lock to a final concentration of 10 mg/mL TA.

Example 17

Visual Comparison of Particles in the Presence and Absence of CSA

Figure 6:
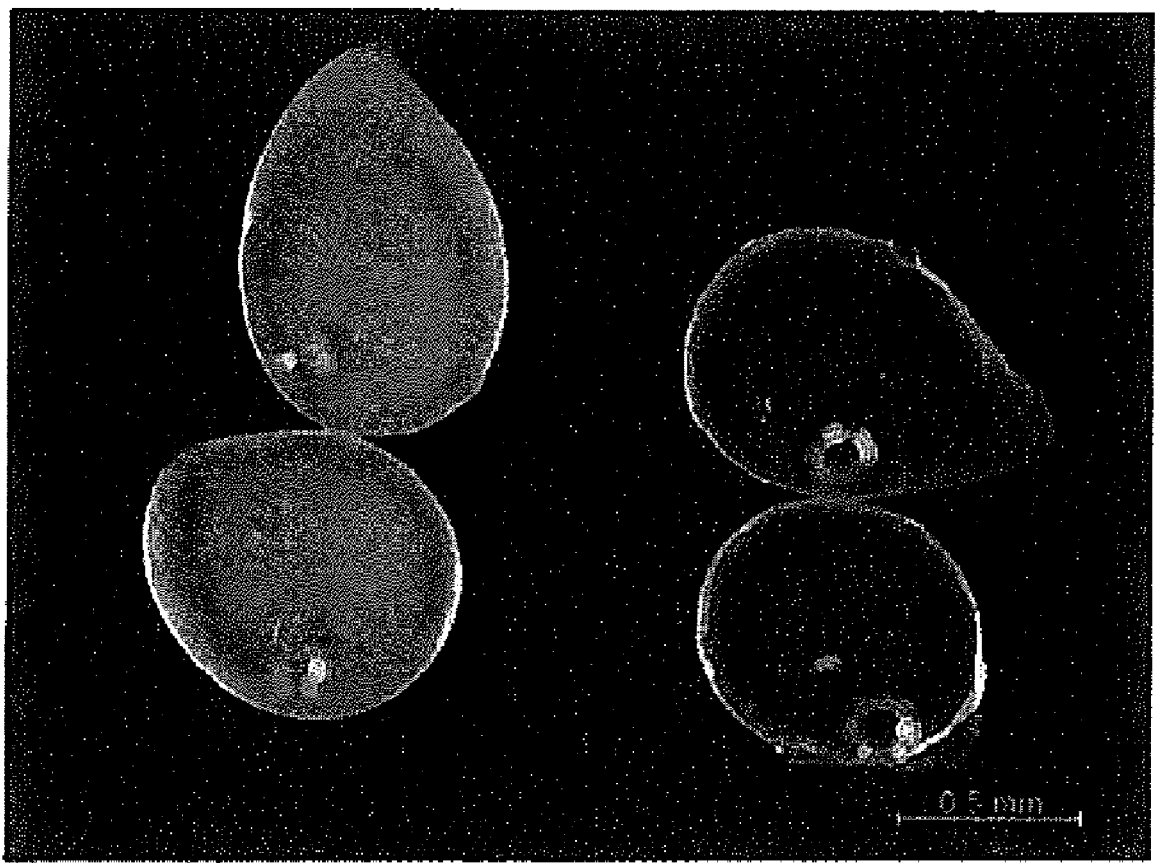
FIG. 6 illustrates CSA loaded chitosan/alginate particles (left) versus non-loaded chitosan/alginate particles (right).

CSA loaded particles were made according to Example 10. For comparison, control particles without CSA were also made according the same general procedure and imaged with a Nikon inverted microscope (FIG. 6). The higher opacity of the CSA loaded particles (FIG. 6, left) that results from the electrostatic interaction between CSA and chitosan provided a visual contrast to the control particles (FIG. 6, right). Furthermore, the size distribution of the particles was varied by controlling the airflow and pump speed. Particles with a diameter range between 10 and 1000 μm were successfully produced using this technique.

Example 18

In-Vitro Release of CSA/TA from HA Filling Gels

CSA is a known hyaluronidase inhibitor that can dramatically decrease the rate of hyaluronic acid degradation. One approach to utilizing this inhibitory potential is to mix CSA with HA. For this purpose samples were prepared according to example 12 and an in vitro CSA release assay was performed.

Figure 7:
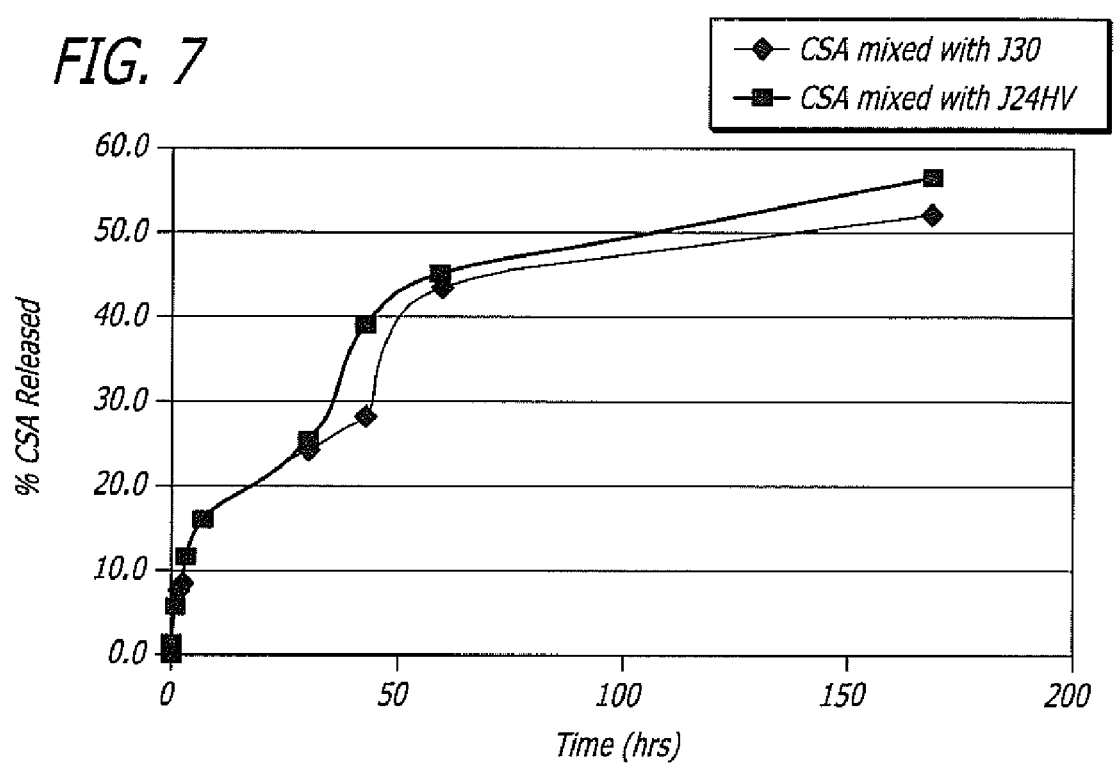
FIG. 7 graphically illustrates In-vitro CSA release from both JUVÉDERM® 30 and JUVÉDERM® 24HV.

CSA/JUVÉDERM® 30 and CSA/JUVÉDERM® 24HV samples were placed into 50 k dialysis bags, each immersed into a stirred PBS solution (pH=7.4). Small samples were occasionally taken from the PBS solution and were analyzed using SEC-MALS to determine the amount of released CSA. The results are summarized in FIG. 7.

Both CSA/JUVÉDERM® 30 and CSA/JUVÉDERM® 24HV samples released approximately 50% of CSA within one week. This fast release was attributed to a number of reasons: the small size of CSA (~20 kDa), the electrostatic repulsion between CSA and HA and the lightly crosslinked HA network, all resulting in a weak retention strength. Simple mixing of CSA with HA was not able to provide a controlled release of CSA that is required for a sustained protection against enzymatic degradation.

Figure 8:
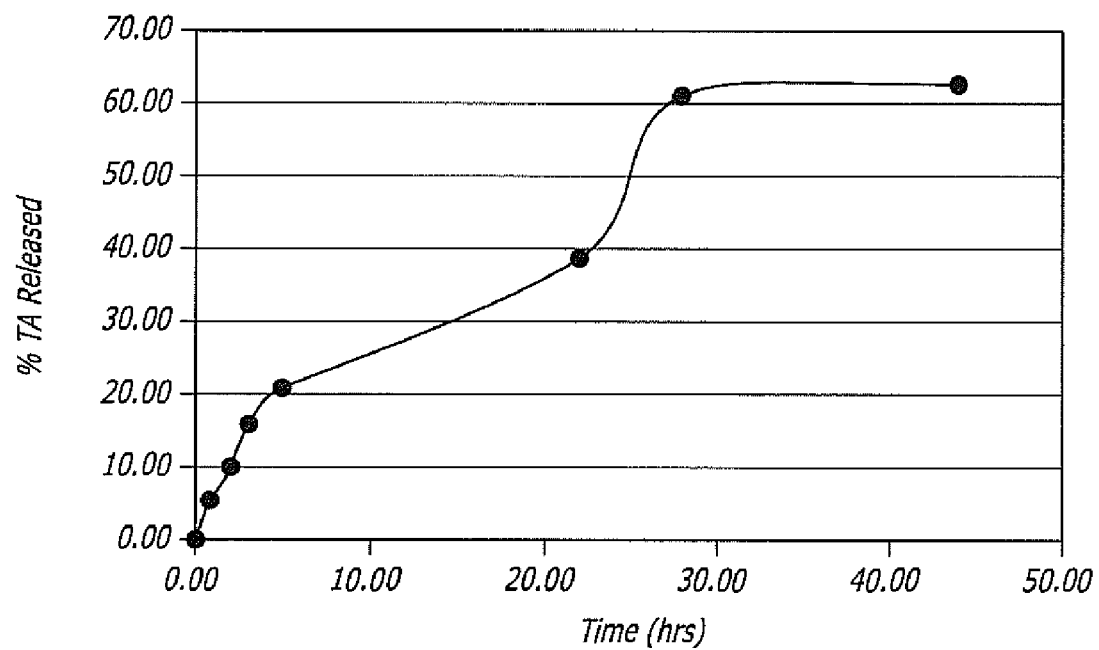
FIG. 8 graphically illustrates In-vitro TA release from JUVÉDERM® 30.

Tannic acid (TA) is an alternative and very potent hyaluronidase inhibitor. One simple approach to utilizing this inhibitory potential is to mix TA with HA. For this purpose, TA was mixed with JUVÉDERM®30 according to Example 16, placed into a 100 k dialysis bag and immersed into a PBS buffer solution. Small samples were occasionally taken from the PBS solution and the TA content was quantified using absorbance measurements. The results are summarized in FIG. 8.

As in the CSA/JUVÉDERM® 30 case, a fast release of TA from the TA/JUVÉDERM® 30 mixture was observed, reaffirming that simple mixing between a small molecule and hyaluronic acid filler gels cannot provide a controlled and sustained release profile.

Example 19

In Vitro Release of CSA/TA from Chitosan Particles

CSA loaded chitosan/alginate particles were prepared according to Example 10, such that the concentration of encapsulated CSA was 5 mg/mL. The sample was placed on an orbital shaker for the length of the test. Samples were periodically taken, filtered through a 0.45 µm filter and injected into a SEC-MALS system. No release of CSA was detected after 2 months. During that time the particles maintained their shape, size and opacity and the buffer solution its clarity.

Figure 9:
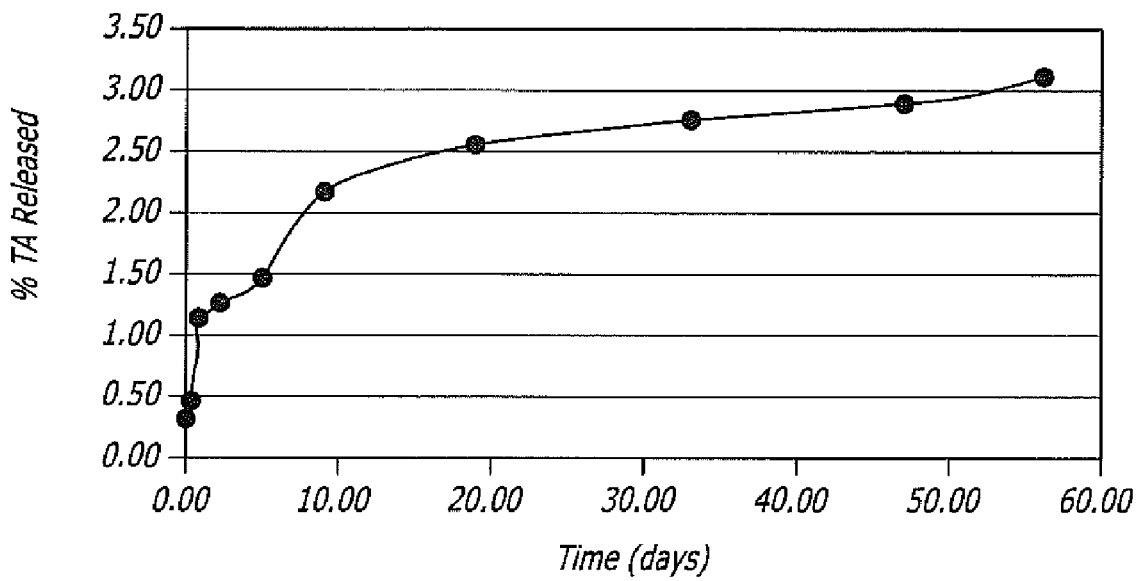
FIG. 9 graphically illustrates in vitro TA release from chitosan/alginate particles.

Similarly TA loaded chitosan/alginate particles were prepared according to Example 14, such that the concentration of encapsulated TA was 1 mg/mL. The sample was placed on an orbital shaker for the length of the test. Samples were periodically taken from the PBS solution and analyzed with absorbance measurements. The absorbance at 314 nm was found to be proportionally related to the amount of TA. The results are summarized in FIG. 9.

Similar to the CSA loaded chitosan/alginate particle case, the release of TA from the chitosan/alginate particles was very slow. This reaffirms that the encapsulation system described herein can provide a slow and sustained release profile of small molecules. This system can be used to deliver inhibitors, antioxidants and other small active molecules in vivo, while maintaining an excellent shelf-stability.

Example 20

In Vitro Release of CSA/TA from Chitosan Particles Mixed with HA Filling Gels

Figure 10:
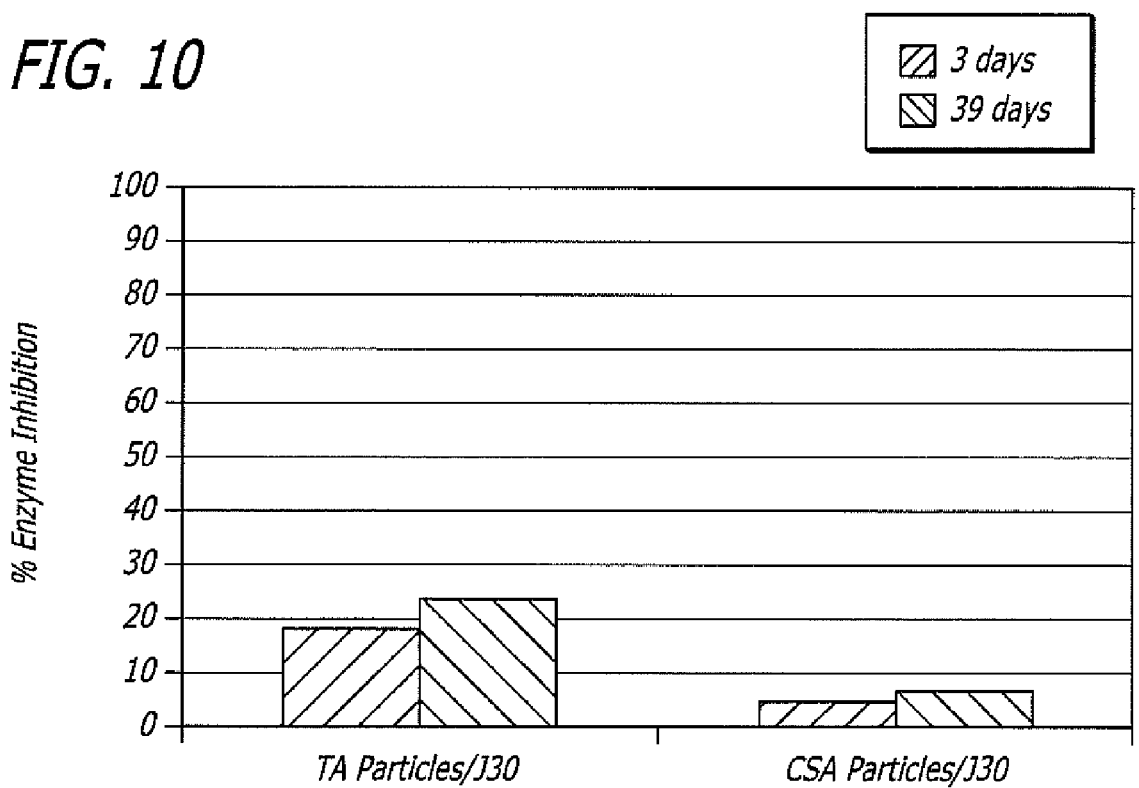
FIG. 10 graphically illustrates inhibition of HA degradation in CSA or TA particle supplemented JUVÉDERM® 30 over time.

CSA loaded chitosan/alginate particles were mixed with JUVÉDERM® 30 according to Example 11. The formulation was thoroughly mixed on a daily basis using two syringes connected via a female-to-female luer-lock and periodically tested using an enzymatic degradation assay: Briefly, hyaluronidase (0.1-10 mg) was added to the formulation, incubated for 10-250 mins at 37° C. followed by addition of 0.1 mL of a 0.8 M potassium tetraborate solution and heating at 100° C. for 10 min. The sample was supplemented with 3 mL of a 10% (wt) p-dimethylaminobenzaldehyde solution in acetic acid and incubated at 37° C. for 10-120 mins. The process was repeated, omitting the enzyme addition, to prepare a control sample. The change in the optical density (OD) at 585 nm between the enzymatically degraded sample and the control sample was used to quantify the extent of degradation. The results were further normalized against the enzymatic performance of an inhibitor free formulation (JUVÉDERM® 30) and summarized in FIG. 10.

TA loaded chitosan/alginate particles were mixed with JUVÉDERM® 30 according to Example 15. The samples were thoroughly mixed on a daily basis using two syringes connected via a female-to-female luer-lock and periodically tested using the enzymatic degradation assay described above. The results are summarized in FIG. 10.

The inhibitory activity of the formulations described above is directly related to the amount of CSA/TA released from the JUVÉDERM® 30 particle system and can be used to gauge the shelf-life of the formulation. It was concluded that following 1 month of storage there was negligible increase in inhibition, suggesting a minor release of CSA/TA from the chitosan/alginate particle-JUVÉDERM® 30 system. This is in agreement with the results in Example 19 and further indicates that the proposed encapsulation system has an excellent shelf-stability.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and, parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A soft tissue augmentation system comprising chondroitin sulfate A (CSA)-containing, alginate-coated chitosan particles dispersed in a cross-linked hyaluronic acid matrix wherein the final concentration of CSA is between about 1 mg/mL and about 10 mg/mL.

2. The soft tissue augmentation system according to claim 1 further comprising lidocaine in the hyaluronic acid matrix.

3. A soft tissue augmentation system comprising chondroitin sulfate A (CSA)-containing, alginate-coated chitosan particles dispersed in a cross-linked hyaluronic acid matrix wherein the final concentration of CSA is between about 1 mg/mL and about 10 mg/mL and wherein said HA matrix further contains from about 1 mg/mL to about 10 mg/mL of tannic acid.

4. The soft tissue augmentation system according to claim 3 further comprising lidocaine in the hyaluronic acid matrix.

5. A soft tissue augmentation system comprising tannic acid-containing, alginate-coated chitosan particles dispersed in a cross-linked hyaluronic acid matrix wherein the final concentration of tannic acid is between about 0.1 mg/mL and about 2 mg/mL.

6. The soft tissue augmentation system according to claim 5 further comprising lidocaine in the hyaluronic acid matrix.

* * * * *

UNITED STATES PATENT AND TRADEMARK OFFICE
CERTIFICATE OF CORRECTION

PATENT NO. : 8,394,784 B2  
APPLICATION NO. : 12/616020  
DATED : March 12, 2013  
INVENTOR(S) : Dimitrios Stroumpoulis et al.

Page 1 of 2

It is certified that error appears in the above-identified patent and that said Letters Patent is hereby corrected as shown below:

On the Title Page, Item (56)

On page 3, in column 1, under "Other Publications", line 9, delete "Viscoelstic" and insert -- Viscoelastic --, therefor.

On page 3, in column 1, under "Other Publications", line 16, delete "Hyroxyethyl" and insert -- Hydroxyethyl --, therefor.

On page 3, in column 2, under "Other Publications", line 51, delete "Institue" and insert -- Institute --, therefor.

On page 3, in column 2, under "Other Publications", line 53, delete "Slerotomy" and insert -- Sclerotomy --, therefor.

On page 4, in column 1, under "Other Publications", line 20, delete "JUVADERM" and insert -- JUVEDERM --, therefor.

On page 4, in column 1, under "Other Publications", line 37, delete "Chrondrocytes" and insert -- Chondrocytes --, therefor.

On page 4, in column 1, under "Other Publications", line 43, delete "Gonarthosis" and insert -- Gonarthrosis --, therefor.

On page 4, in column 1, under "Other Publications", line 53, delete "An Theum" and insert -- Ann Rheum --, therefor.

On page 4, in column 2, under "Other Publications", line 4, delete "Intral-" and insert -- Intra- --, therefor.

On page 4, in column 2, under "Other Publications", line 7, delete "Falling" and insert -- Filling --, therefor.

Signed and Sealed this  
Seventh Day of October, 2014

Michelle K. Lee  
*Deputy Director of the United States Patent and Trademark Office*

CERTIFICATE OF CORRECTION (continued)
U.S. Pat. No. 8,394,784 B2

On page 4, in column 2, under "Other Publications", line 20, delete "Rheuymatism" and insert -- Rheumatism --, therefor.

On page 4, in column 2, under "Other Publications", line 21, delete "Collegen" and insert -- Collagen --, therefor.

On page 4, in column 2, under "Other Publications", line 22, after "Release" insert -- Rate --.

On page 4, in column 2, under "Other Publications", line 30, delete "Idiopathis" and insert -- Idiopathic --, therefor.

On page 4, in column 2, under "Other Publications", line 38, delete "Matierals" and insert -- Material --, therefor.

On page 4, in column 2, under "Other Publications", line 40, delete "Influcence" and insert -- Influence --, therefor.

On page 4, in column 2, under "Other Publications", line 41, delete "Chemical-" and insert -- Chemico- --, therefor.

On page 4, in column 2, under "Other Publications", line 47, delete "Crosslinkedwith" and insert -- Crosslinked with --, therefor.

On page 4, in column 2, under "Other Publications", lines 47-48, delete "Glyol Tetracrylates" and insert -- Glycol Tetraacrylates --, therefor.

In the Specification

In column 6, line 30, delete "GSA" and insert -- CSA --, therefor.

In column 6, line 48, delete "amylocalne," and insert -- amylocaine, --, therefor.

In column 6, line 52, delete "dicyclonine," and insert -- dicyclomine, --, therefor.

In column 6, line 58, delete "octacaine," and insert -- octocaine, --, therefor.

In column 7, line 44, delete "abut" and insert -- about --, therefor.

In column 9, line 65, delete "flavanols," and insert -- flavonols, --, therefor.

In column 12, line 52, delete "GSA" and insert -- CSA --, therefor.